United States Patent [19]

Fischer et al.

[11] 4,167,300

[45] Sep. 11, 1979

[54] MEASURING ELECTRODE, ESPECIALLY GLASS ELECTRODE

[75] Inventors: Walter W. Fischer, Morges; Peter Jucker, Zug; Werner Ingold, Uitikon, all of Switzerland

[73] Assignee: Proton AG, Zug, Switzerland

[21] Appl. No.: 758,139

[22] Filed: Jan. 10, 1977

[30] Foreign Application Priority Data

Jan. 14, 1976 [CH] Switzerland ............... 406/76

[51] Int. Cl.² .................................. H01R 13/00
[52] U.S. Cl. .......................... 339/94 C; 339/177 R
[58] Field of Search .................... 204/195 G, 195 R; 324/29, 30 R; 339/177 R, 88, 89 C, 90 R, 94 C, 177 E

[56] References Cited

U.S. PATENT DOCUMENTS

| | | | |
|---|---|---|---|
| 2,673,233 | 3/1954 | Salisbury | 339/177 R X |
| 2,762,025 | 9/1956 | Melcher | 339/177 R X |
| 2,785,384 | 3/1957 | Mickesser | 339/94 C |
| 3,107,135 | 10/1963 | Keil | 339/94 C |
| 3,111,356 | 11/1963 | Mazzagatti et al. | 339/177 R X |
| 3,343,122 | 9/1967 | Drogo | 339/177 R |
| 3,476,672 | 11/1969 | Snyder et al. | 204/195 G |
| 3,879,102 | 4/1975 | Horak | 339/177 R |
| 3,936,132 | 2/1976 | Hutter | 339/177 R |
| 4,008,141 | 2/1977 | Katoni et al. | 204/195 G |

FOREIGN PATENT DOCUMENTS

| | | | |
|---|---|---|---|
| 497612 | 5/1930 | Fed. Rep. of Germany | 339/177 R |
| 204706 | 10/1924 | United Kingdom | 339/177 R |
| 428490 | 1/1975 | U.S.S.R. | 339/177 R |

Primary Examiner—Joseph H. McGlynn
Attorney, Agent, or Firm—Werner W. Kleeman

[57] ABSTRACT

A measuring electrode, especially a glass electrode, having a body detachably connected by means of a coaxial connection device with a connection cable. The part of the connection device arranged at the body is constructed as a plug portion and its inner plug and coaxially arranged outer plug are separated from one another by means of an insulating body. The outer plug is axially rearwardly set back in relation to the end of the insulating body of the plug portion. An insulating body of a bushing portion of the connection device engages in a cap-like manner over the free part of the insulating body of the plug portion.

24 Claims, 3 Drawing Figures

MEASURING ELECTRODE, ESPECIALLY GLASS ELECTRODE

BACKGROUND OF THE INVENTION

The present invention relates to a new and improved construction of a measuring electrode, especially a glass electrode, the body of which is detachably connected by means of a coaxial connection device with a connection cable, and wherein the part of the connection device arranged at the body is constructed as a plug portion and its inner plug and coaxially arranged outer plug are separated from one another by means of an insulating body.

A measuring electrode of the previously mentioned type has been disclosed, for instance, in U.S. Pat. No. 3,476,672. The outer plug comprises a metallic sleeve extending up to the end face of the insulating body, so that there only is present a short insulating path between the inner plug and the metallic sleeve of the outer plug. Thus, the connection device tends to form short-circuits, especially when the measuring electrode, with the connection cable removed, is sterilized at 130° C. in a vapor or steam injector. This is especially so because, when working with a vapor injector, the treatment vessel to be sterilized together with the measuring electrode is initially evacuated, then exposed to a vapor surge at elevated temperatures, and, upon cooling and removal from the vapor injector, condensate forms. This condensate builds short-circuit bridges at the short insulation path.

SUMMARY OF THE INVENTION

Hence, it is a primary object of the present invention to provide a new and improved construction of measuring electrode, especially a glass electrode, which is not associated with the aforementioned drawbacks and limitations of the prior art constructions.

Now in order to implement this object and others which will become more readily apparent as the description proceeds, the measuring electrode of the present development is manifested by the features that the outer plug is axially rearwardly set back relative to the end of the insulating body of the plug portion and an insulating body of a bushing portion engages in the manner of a cap over the free part of the insulating body of the plug portion.

By virtue of the fact that the outer plug of the connection device is axially rearwardly set back with respect to the end face of the insulating body of the plug portion, the insulating path is considerably lengthened and there is thus reduced the danger of forming short-circuit bridges. Due to the free edge of the insulating body and the cap-like covering of the free part of the insulating body of the plug portion by the insulating body of the bushing portion, there is also practically completely suppressed the formation of a short-circuit bridge. Consequently, the connection device possesses faultless electrical properties following sterilization, even in the presence of moist sterilization conditions, high temperatures and changing pressures.

The measuring electrode can be of random construction, and it is preferably designed as a glass electrode or a redox electrode.

BRIEF DESCRIPTION OF THE DRAWING

The invention will be better understood and objects other than those set forth above, will become apparent when consideration is given to the following detailed description thereof. Such description makes reference to the annexed drawings.

DETAILED DESCRIPTION OF THE PREFERRED EMBODIMENTS

Figure 1:
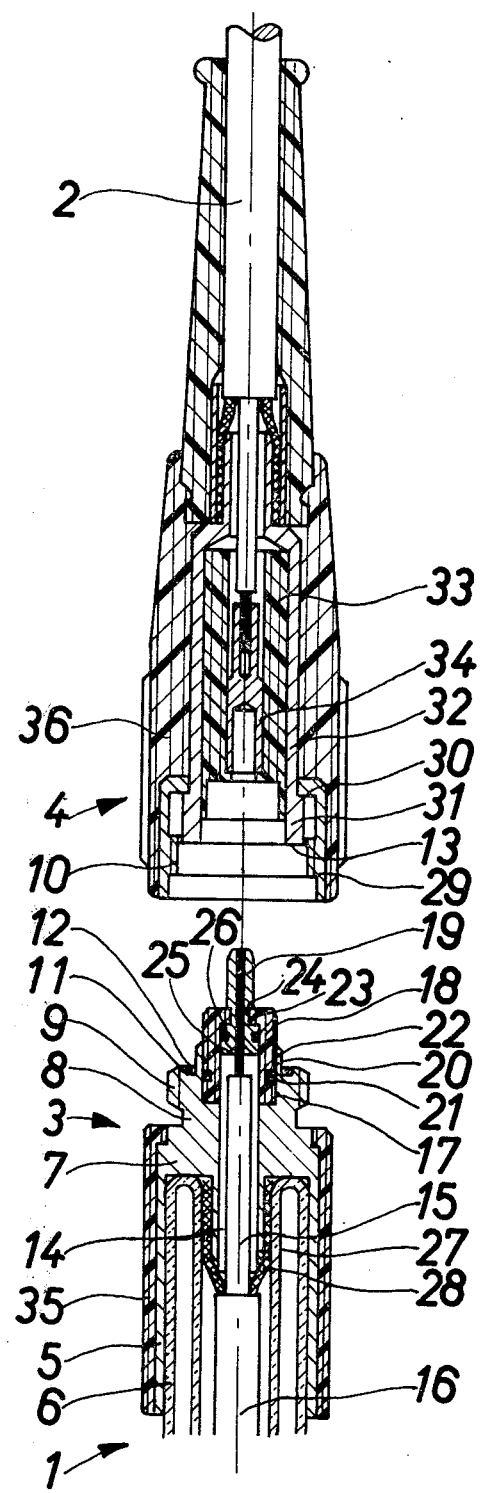
FIG. 1 illustrates a preferred exemplary embodiment of the measuring electrode constructed according to the present invention, and shows the connection device of the measuring electrode in exploded longitudinal sectional view.
Figure 2:
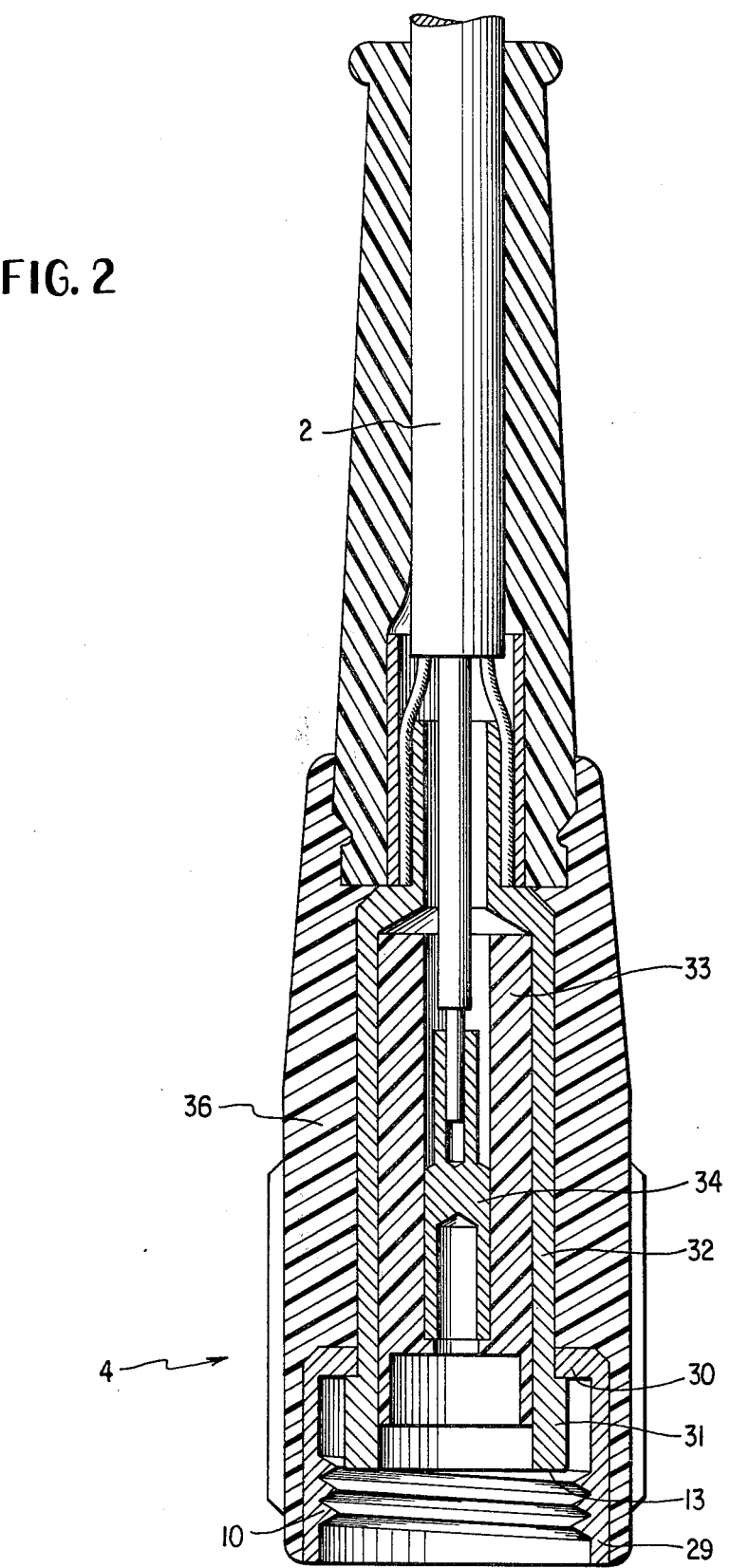
FIG. 2 illustrates the plug portion secured to the glass electrode.
Figure 3:
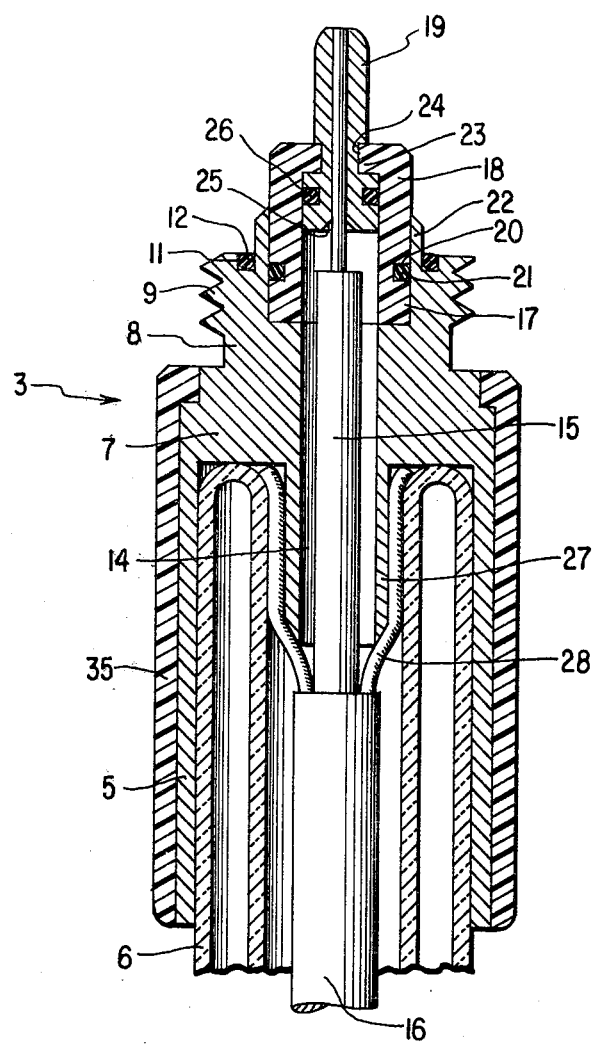
FIG. 3 illustrates the cooperating bushing portion arranged at the connection cable.

Describing now the drawings, the exemplary illustrated embodiment of the measuring electrode will be seen to comprise a glass electrode 1 which is detachably connected by means of a coaxial connection device with a connection cable 2. To this end the coaxial connection device contains a plug portion or part 3 arranged at the glass electrode, this plug portion 3 cooperating with a bushing portion or part 4 arranged at the connection cable 2.

The plug portion 3 secured to the glass electrode 1 will be understood to first of all comprise an outer plug 5 constructed as a metallic sleeve and adhesively bonded to the glass body 6 of the glass electrode 1. The outer plug 5 is equipped with a floor or base portion 7 containing a substantially coaxially protruding outer projection or extension 8 carrying a suitable connection means or element, such as external threading 9 which coacts with connection means in the form of internal threading 10 provided at the bushing portion 4 of the connection cable 2. Of course, connection means or elements other than cooperating threaded parts can be provided, and thus, the components 9 and 10 can be, for instance, conceptually construed to comprise a bayonet-type connection. At the end or end face of the outer projection 8 a sealing ring 12 is preferably arranged in a substantially ring-shaped or annular groove 11, the sealing ring 12 contacting an end surface 13 of the bushing portion 4.

The base portion 7 of the outer plug 5 contains a continuous coaxial bore 14 for the reception of the internal or inner conductor 15 of a coaxial cable 16 of the glass electrode 1. This bore 14 possesses a substantially cylindrical widened portion or enlargement 17 at the part thereof facing away from the glass electrode 1. At the widened or enlarged portion 17 there is attached a substantially cylindrical insulating body 18 which coaxially carries a metallic inner plug 19 for the inner conductor 15. In the illustrated exemplary embodiment the insulating body 18 is connected by way of example, on the one hand, by a press fit in the enlarged or widened portion 17 and, on the other hand, the inner plug 19 is connected by a press or force fit in the insulating body 18. The plug portion 3 is constructed such that the outer plug 5 is axially rearwardly set back in relation to the end face or end of the insulating body 18.

In order to improve the sealing action and the connection of the insulating body 18 with the base portion 7, the insulating body 18 carries at its outer surface, preferably within a continuous groove 20, a sealing ring 21 which cooperates with the inner wall of the cylindrical widened portion 17. The base portion 7 furthermore is of substantially round configuration and the widened portion 17 is equipped with an axially protruding flange 22 which is extends in the direction of the insulating body 18.

In order to improve the attachment of the inner plug 19 at the insulating body 18, the latter contains a radially extending inner flange 23 which engages in a groove 24 provided at the inner plug 19. The inner plug 19 furthermore carries at its outer surface, preferably in a continuous groove of an outer flange 25 thereof, a sealing ring 26 which cooperates with the inner surface of the insulating body 18.

The insulating body 18 of the plug portion 3 is formed of a material possessing a good total resistance, i.e., a good internal and surface resistance. Insulating body 18 is preferably formed of plastic, and polytrifluorochloroethylene has been found to be especially suitable. If desired there also can be used ceramic materials or glass.

The base portion 7 contains an axially inwardly protruding substantially cylindrical inner projection or extension 27 arranged about the bore 14, and at the outer surface of which there is attached the outer conductor 28 of the coaxial cable 16.

The bushing portion 4 contains an outer bushing or sleeve 29 carrying the inner threading 10 or other suitable connection means. Furthermore, it is equipped with an inner flange 30 which bears against an outer flange 31 of a sleeve 32 which, by means of an insulating body 33, carries an inner bushing or sleeve 34 into which engages the inner plug 19 of the plug portion or part 3. The sleeve 32 by means of its outer flange 31 forms the end surface or face 13 at which bears the sealing ring 12 of the plug portion 3. The bushing portion or part 4 is constructed in such a manner that its insulating body 33 engages in a cap-like manner over the free part or end of the insulating body 18 of the plug portion 3.

Both the plug portion 3 as well as the bushing portion 4 are provided with an insulating covering 35 and 36 respectively.

In contrast to the exemplary illustrated embodiment there are possible many different constructional changes for the measuring electrode. Thus, for instance, the outer projection 8 of the plug portion 3, as mentioned, can support a bayonet connection part instead of the outer threading 9 which, then, cooperates with a corresponding bayonet connection part of the bushing portion 4. Also, it is possible to connect the insulating body 18, instead of by means of a press fit, through the agency of a thread connection on the one hand with the enlarged or widened portion 17 and, on the other hand, with the plug 19. Such thread connection or press fit, if desired, also can be augmented by using an adhesive connection, which insures for an increased sealing action.

While there are shown and described present preferred embodiments of the invention, it is to be distinctly understood that the invention is not limited thereto, but may be otherwise variously embodied and practiced within the scope of the following claims.
ACCORDINGLY,

What we claim is:

1. A cable connection system for a measuring electrode for detachably connecting a body of the measuring electrode with a connection cable, comprising:

a part arranged at the body which is constructed as a plug portion;

said plug portion comprising an inner plug and a substantially coaxially arranged outer plug separated from one another by an insulating body having an end face;

said outer plug being axially rearwardly set back from the end face of the insulating body;

said connection device further comprising a bushing portion having an insulating body;

said insulating body of the bushing portion engaging in a substantially cap-like manner over a free part of the insulating body of the plug portion said free part of said insulating body of the plug portion provides a relatively large insulation path separating the inner plug and the coaxially arranged outer plug, which large path counteracts the formation of short-circuit bridges both by arcing and by possible vapor condensate deposition thereat; and said free part of said insulating body includes a free edge between an end surface thereof and an outer peripheral portion thereof which free edge promotes tear-off of any condensate film formed thereat when said plug portion is engaged with said bushing portion.

2. The cable connection system as defined in claim 1, wherein:

said outer plug comprises a metallic sleeve which is secured to said body.

3. The cable connection system as defined in claim 1, wherein:

said insulating body of the plug portion is formed of a ceramic material.

4. The cable connection system as defined in claim 1, wherein:

said insulating body of the plug portion is formed of glass.

5. The cable connection system as defined in claim 1, wherein:

said outer plug includes a base portion having a substantially coaxially protruding outer projection;

said coaxially protruding outer projection and said bushing portion possessing cooperating connecting means for interconnecting the coaxially protruding outer projection with the bushing portion.

6. The cable connection system as defined in claim 5, wherein:

said connecting means comprise external threading provided for said outer projection and said bushing portion comprising an outer bushing having internal threading.

7. The cable connection system as defined in claim 5, wherein:

said connecting means comprises first bayonet connecting means provided for said outer projection and second bayonet connection means provided for said bushing portion for interconnecting said outer projection with said bushing portion.

8. The cable connection system as defined in claim 5, wherein:

said bushing portion possesses an outer sleeve having an inner flange;

an inner sleeve having an outer flange;

said inner flange bearing against the outer flange of said inner sleeve;

said inner sleeve carrying by means of the insulating body of the bushing portion an inner bushing of said bushing portion.

9. The cable connection system as defined in claim 5, wherein:
   said bushing portion is provided with an end surface;
   said outer projection having an end face at which there is arranged a sealing ring;
   said sealing ring bearing against the end surface of the bushing portion.

10. The cable connection system as defined in claim 9, wherein the outer projection is provided with a substantially ring-shaped groove containing said sealing ring.

11. The cable connection system as defined in claim 9, wherein:
   said base portion of the outer plug possesses a continuous coaxial bore for the reception of an inner conductor of a coaxial cable of the measuring electrode;
   said bore having a part facing away from the measuring electrode possessing a substantially cylindrical widened portion for the reception of said insulating body of the plug portion;
   said bushing portion including a sleeve having an outer flange;
   said sealing ring of the outer projection of the plug portion bearing against an end surface of said outer flange of said sleeve of the bushing portion.

12. The cable connection system as defined in claim 5, wherein:
   said base portion of the outer plug is provided with a continuous substantially coaxial bore for the reception of an inner conductor of a coaxial cable of the measuring electrode;
   said bore being provided at a part thereof facing away from the measuring electrode with a substantially cylindrical widened portion for the reception of said insulating body of the plug portion.

13. The cable connection system as defined in claim 12, wherein:
   said base portion possesses a substantially axially protruding flange extending around the widened portion;
   said axially protruding flange extending in the direction of the insulating body of the plug portion.

14. The cable connection system as defined in claim 12, wherein:
   said insulating body of the plug portion is secured by a press fit at the base portion and the inner plug by a press fit at such insulating body.

15. The cable connection system as defined in claim 12, wherein:
   the insulating body of the plug portion is secured by an adhesive bond at the base portion and the inner plug is secured by an adhesive bond at such insulating body.

16. The cable connection system as defined in claim 12, further including:
   means for securing the insulating body of the plug portion at the base portion and the inner plug at such insulating body.

17. The cable connection system as defined in claim 12, wherein:
   said base portion possesses an axially inwardly protruding, substantially cylindrical inner projection arranged about said bore;
   said inner projection having an outer surface at which there is attached an outer conductor of the coaxial cable.

18. The cable connection system as defined in claim 12, further including:
   a sealing ring supported by the insulating body of the plug portion at an outer surface thereof;
   the substantially cylindrical widened portion of the base portion of the outer plug having an inner wall with which cooperates said sealing ring.

19. The cable connection system as defined in claim 18, wherein:
   said insulating body of the plug portion is provided at its outer surface with a continuous groove carrying said sealing ring.

20. The cable connection system as defined in claim 18, wherein:
   said base portion is provided with an axially protruding flange extending about the widened portion,
   said axially protruding flange extending in the direction of the insulating body of the plug portion.

21. The cable connection system as defined in claim 1, wherein:
   said insulating body of the plug portion possesses a radial inner flange;
   said inner plug being provided with a groove;
   said radial inner flange engaging with said groove of said inner plug.

22. The cable connection system as defined in claim 21, wherein:
   said inner plug possesses an outer flange arranged within the insulating body of the plug portion;
   said outer flange bearing by means of a sealing ring axially at said inner flange of the insulating body.

23. The cable connection system as defined in claim 1, wherein:
   said insulating body of the plug portion is formed of plastic.

24. The cable connection system as defined in claim 23, wherein:
   said plastic is polytrifluorochloroethylene.

* * * * *